(12) United States Patent
Andersen et al.

(10) Patent No.: US 11,583,215 B2
(45) Date of Patent: Feb. 21, 2023

(54) GENERIC EAR DEVICE WITH ELECTRODES

(71) Applicant: T&W Engineering A/S, Lynge (DK)

(72) Inventors: Mikael Andersen, Alleroed (DK); Mike Lind Rank, Farum (DK); Hans Olaf Toft, Frederiksberg C (DK); Preben Kidmose, Maarslet (DK); Simon Lind Kappel, Mt. Lavinia (LK)

(73) Assignee: T&W Engineering A/S, Lynge (DK)

( * ) Notice: Subject to any disclaimer, the term of this patent is extended or adjusted under 35 U.S.C. 154(b) by 807 days.

(21) Appl. No.: 16/430,639

(22) Filed: Jun. 4, 2019

(65) Prior Publication Data
US 2019/0282119 A1   Sep. 19, 2019

Related U.S. Application Data

(63) Continuation of application No. PCT/EP2016/080447, filed on Dec. 9, 2016.

(51) Int. Cl.
*A61B 5/00* (2006.01)
*H04R 25/00* (2006.01)
(Continued)

(52) U.S. Cl.
CPC .............. *A61B 5/291* (2021.01); *A61B 5/30* (2021.01); *A61B 5/6815* (2013.01);
(Continued)

(58) Field of Classification Search
CPC ......... A61B 5/291; A61B 5/30; A61B 5/6815; A61B 5/6817; A61B 5/316; A61B 5/398;
(Continued)

(56) References Cited

U.S. PATENT DOCUMENTS

| 706,682 A | 11/1987 | Stypulkowski et al. |
| 7,899,200 B2 * | 3/2011 | Karamuk ............. H04R 25/656 |
| | | 381/328 |

(Continued)

FOREIGN PATENT DOCUMENTS

| CN | 105705119 A | 6/2016 |
| CN | 205697764 U | 11/2016 |

(Continued)

OTHER PUBLICATIONS

Written Opinion of the International Searching Authority of PCT/EP2016/080447 dated Aug. 31, 2017.

(Continued)

*Primary Examiner* — Oyesola C Ojo
(74) *Attorney, Agent, or Firm* — Sughrue Mion, PLLC

(57) ABSTRACT

An ear device for arrangement at an ear of a person and provided with at least two electrodes for having skin contact and detecting a bioelectrical signal when in use, the ear device includes a deformable ear canal part adapted to be arranged in an ear canal of the person, and an external ear part adapted to be arranged at the ear external to the ear canal and being provided with at least one external ear electrode for detecting a bioelectrical signal, the external ear part includes at least one bendable arm which is connected to the ear canal part and is adapted to exert a pressure such that the at least one external ear electrode is pressed against the skin when in use.

23 Claims, 9 Drawing Sheets

(51) Int. Cl.
*A61B 5/291* (2021.01)
*A61B 5/30* (2021.01)
A61B 5/316 (2021.01)
A61B 5/398 (2021.01)

(52) U.S. Cl.
CPC ............ *A61B 5/6817* (2013.01); *A61B 5/316* (2021.01); *A61B 5/398* (2021.01); *A61B 5/7207* (2013.01); *A61B 2560/0425* (2013.01); *H04R 25/652* (2013.01); *H04R 2225/77* (2013.01)

(58) Field of Classification Search
CPC .......... A61B 5/7207; A61B 2560/0425; H04R 25/652; H04R 2225/77
See application file for complete search history.

(56) References Cited

U.S. PATENT DOCUMENTS

| | | | | |
|---|---|---|---|---|
| 2006/0094974 | A1* | 5/2006 | Cain | A61B 5/291 600/545 |
| 2007/0080817 | A1* | 4/2007 | Grilliot | G08B 3/10 340/584 |
| 2007/0112277 | A1* | 5/2007 | Fischer | A61B 5/6817 600/544 |
| 2008/0123888 | A1* | 5/2008 | Schanz | H04R 25/656 381/328 |
| 2008/0165017 | A1* | 7/2008 | Schwartz | A61B 5/486 600/324 |
| 2009/0052702 | A1* | 2/2009 | Murphy | H04R 1/1016 381/380 |
| 2009/0252362 | A1* | 10/2009 | Ooi | H04R 25/65 264/222 |
| 2010/0239114 | A1* | 9/2010 | Wada | A61B 5/6817 381/380 |
| 2010/0303275 | A1* | 12/2010 | Creek | A61F 11/06 381/380 |
| 2010/0331660 | A1* | 12/2010 | Wada | A61B 5/6817 600/382 |
| 2013/0184552 | A1 | 7/2013 | Westermann et al. | |
| 2013/0296731 | A1* | 11/2013 | Kidmose | A61B 5/6833 600/544 |
| 2014/0140567 | A1 | 5/2014 | Leboeuf et al. | |
| 2014/0171775 | A1 | 6/2014 | Kilsgaard et al. | |
| 2014/0235967 | A1* | 8/2014 | LeBoeuf | A61B 5/4806 600/300 |
| 2014/0288447 | A1* | 9/2014 | Luna | A61B 5/6838 600/508 |
| 2015/0139474 | A1 | 5/2015 | Henry et al. | |
| 2015/0215693 | A1* | 7/2015 | Sandanger | H04R 1/1083 381/380 |
| 2016/0199203 | A1* | 7/2016 | Adachi | A61F 4/00 600/383 |
| 2019/0223747 | A1* | 7/2019 | Chou | A61B 5/4812 |

FOREIGN PATENT DOCUMENTS

| | | |
|---|---|---|
| WO | 2007/047667 A2 | 4/2007 |
| WO | 2011/000383 A1 | 1/2011 |

OTHER PUBLICATIONS

International Search Report of PCT/EP2016/080447 dated Aug. 31, 2017.

Office Action dated May 11, 2022 from the China National Intellectual Property Administration in CN Partial Application No. 201680091993.5.

* cited by examiner

GENERIC EAR DEVICE WITH ELECTRODES

CROSS-REFERENCE TO RELATED APPLICATIONS

This application is a continuation of PCT International Application No. PCT/EP2016/080447 filed Dec. 9, 2016, the disclosure of which is incorporated by reference herein.

BACKGROUND OF THE INVENTION

The present invention relates to an ear component for detecting bioelectrical signals. The invention relates more particularly to an ear component for arrangement partly in an ear canal and partly at the ear outside the ear canal (e.g. in the concha region, and/or in a region behind the ear).

Bioelectrical signals are here understood to be electrical potential differences originating from a living body. Well-known examples are Electrocardiogram (ECG) signals and Electroencephalogram (EEG) signals. An ear component for detecting bioelectrical signals at the ear is often made for the detection of EEG signals, but could also be applied for detecting other bioelectrical signals such as ECG, electrooculography (EOG), or muscular activity.

EEG signals are electrical signals generated by a person's brain activity. In recent years, EEG monitoring systems, that may be carried or worn continuously by a person to be monitored, have been devised. A goal is to have personal wearable EEG monitors, which can be carried without causing more inconvenience than glasses or a modern small hearing aid, even when carried over several months or years.

Such EEG monitors may be applied for different purposes. One example is surveillance of a condition of a person and e.g. for providing an alarm or information in case predetermined conditions are met. The monitor may also be applied for collection of data, e.g. for diagnostic purposes or for research use. Examples of applications are for surveillance of persons having diabetes or epilepsy. Another example is as input to the control or adjustment of a hearing aid.

Moreover, in recent years there has been a lot of activities within transcranial neuro-stimulation (e.g. tDCS and tACS). Here, electrodes are used for recording electrical signals, but also for neuro-stimulation. Another application could be measurement of galvanic skin-responses (GSR).

Furthermore, electric potentials originating from neural activity in the cranial nerves and in the brain stem may also be measured with ear devices. This is e.g. relevant in assessment of hearing loss, where it is common to measure responses from the cranial nerve (cranial nerve 8) and from the brain stem (as in auditory brain stem responses). But it may also be relevant to measure responses from e.g. the vagus nerve (cranial nerve 10) which have branches out in the external ear. This may e.g. be of relevance in epilepsies.

Measuring the EEG signal in the ear canal is known from WO 2011/000383 A1 disclosing an ear plug with EEG electrodes where the ear plug shape is individually matched or customized to the users ear canal.

WO 2007/047667 A2 discloses an ear plug made from a compressible material and provided with EEG ear canal electrodes. External ear electrodes are arranged on a measurement device, which is worn behind the ear. Thereby, the housing of the measurement device is shaped/customized to the curved contour of the ear of an individual.

SUMMARY OF THE INVENTION

One problem with the known solutions is that a customization of the ear plug to the ear canal of the individual user or of the housing of the measurement device to the curved contour of the ear of the individual user is necessary, which produces high costs. It takes time to manufacture customized ear-pieces. First a 3D model must be obtained based on an ear-impression or ear-scanning. Second the individual ear-piece must be modelled and manufactured. This has several consequences: (a) Need for infrastructure (3D-scanners, manufacturing setup for single-device manufacturing, etc.) and trained personal, which is also costly. (b) The user/patient must show up at least twice in the clinic: first to get the ear-impression taken, and second to get the device. This is inconvenient and costly. (c) The time-consuming and cumbersome process is prohibitive for some applications, e.g. for applications where it is intended to measure for a short period of time. One example could be in cases where it is intended to monitor sleep over a few days or weeks. Another example could be in an intensive care unit (ICU) or in an emergency situation. Moreover, customized parts do not necessarily guarantee a satisfying bioelectrical signal in case of ear form changes (e.g. speech, during sleep, etc.), movement of the housing of the measurement device, and/or jaw movements, which are the most severe source for motion artefacts in ear-EEG devices.

The present invention is thus directed to provide an ear device for detecting bioelectrical signals at low costs and at short time scales, whereby the ear device constantly delivers satisfying bioelectrical signals when in use.

The present invention is defined in claim 1. Preferred embodiments are defined in the dependent claims.

A solution to the above problem has been found by an ear device for arrangement at an ear of a person and provided with at least two electrodes for having skin contact and detecting a bioelectrical signal when in use, the ear device comprises a deformable ear canal part adapted to be arranged in an ear canal of the person, and an external ear part adapted to be arranged at the ear external to the ear canal and being provided with at least one external ear electrode for detecting a bioelectrical signal, the external ear part comprises at least one bendable arm which is connected to the ear canal part and is adapted to exert a pressure such that the at least one external ear electrode is pressed against the skin when in use.

One advantage of the solution is that a customization of the ear device is not necessary due to the deformable ear canal part and the bendable arm. In other words, generic ear canal parts and generic bendable arms can be used for different users. This significantly reduces the time it takes to adapt a device, makes it less cumbersome for both dispenser and user, requires less infrastructure and less training of personal, and in consequence reduces cost. Furthermore, a user may use the ear device immediately, which saves time and is cost-efficient. Moreover, the deformable ear canal part as well as the bendable arm constantly press against the skin when in use such that a satisfying contact between the electrodes and the skin is provided. Even when the form of the ear changes (e.g. during sleeping), the elastic properties of the deformable ear canal part and the bendable arm compensate said form change such that a constant contact of the electrodes with the skin is provided, which thus constantly delivers satisfying bioelectrical signals when in use. Further advantages of the claimed subject-matter are: Easy to adapt to the individual ear, good and reliable electrode contact, high comfort, easy to use (user-friendly) and unobtrusive to normal life activities, no occlusion of the ear. Thereby, the ear canal part further stabilizes the position of the external ear part. Moreover, different materials for the ear canal part and the external ear part may be used, preferably rubber, silicone, compounds of different shore hardness, etc.

According to a further embodiment, the ear canal part is provided with at least one ear canal electrode for detecting a bioelectrical signal, the at least one ear canal electrode is arranged at a structure adapted to be deformed when the ear canal part is arranged in an ear canal, such that the at least one ear canal electrode is pressed against the skin of the ear canal. Thereby, the measurement of the bioelectrical signals may be based on the ear canal part and the external ear part. Due to the distance between these two parts, the measurement quality of the bioelectrical signals is further improved in comparison with a measurement of the bioelectrical signals based only on the ear canal part.

According to a further embodiment, the ear canal part is formed such that it only has contact to an upper part of the ear canal when in use. Thereby, the force applied to the upper part of the ear canal is then balanced by an opposing force from the external ear part. This embodiment provides several advantages: (a) The upper part (superior) of the ear canal is the most shape-stable part of the ear-canal because it is following the shape of the skull. The bottom part (inferior) and the sides (posterior and anterior) are to a large extent influenced by the position of the jaw. Therefore, the upper part is less influenced by jaw movements, and consequently less prone to motion artefacts. (b) The upper part of the ear canal is closer to the brain, and therefore electrodes in the upper part may be better for EEG signal recording. (c) In most applications it is desirable to have an acoustical transparent device. By minimizing the size of the ear canal part there will be less occlusion.

According to a further embodiment, at least a part of the bendable arm is a concha part adapted to be arranged in a concha region of the ear and further adapted to follow the shape of the concha. The concha region is highly suitable to receive the bendable arm. The bendable arm can thus easily and securely press against the protrusions of the concha region (e.g. the antehelix), whereby a secure fixing of the bendable arm and thus an improved contact between the external ear electrode and the skin is provided. Thereby, the bendable arm is preferably extending from the ear canal part to at least a point in the concha, where the at least one external ear electrode is held.

According to a further embodiment, the bendable arm may comprise a cutoff portion, which is removable from the bendable arm. Thereby, the bendable arm purposefully is made too long, and the bendable arm can easily be shortened for example by cutting with a scissor. This facilitates the fitting of one ear device to a multitude of users.

According to a further embodiment, at least a part of the bendable arm is a tragus part adapted to be arranged in a tragus region of the ear and further adapted to follow the shape of the tragus, wherein preferably the bendable arm is extending from the ear canal part to at least a point at the tragus, where the at least one external ear electrode is held. The tragus region of the ear is preferred since this region allows for extra pressure without compromising comfort. This can be achieved by adding additional material to the bendable arm. Moreover, the tragus region often has a different potential than the concha region, as shown by measurements. This further improves the measurement of the bioelectrical signal.

According to a further embodiment, the ear device comprises a detachable connection to a unit holding a bioelectrical signal processor and a power supply. Thereby, the ear device can easily be connected to said unit.

According to a preferred embodiment, the bioelectrical signal is an EEG signal.

According to a preferred embodiment, the bendable arm is adapted to hold the at least one external ear electrode. When the at least one external ear electrode is directly arranged on the bendable arm, a particularly good contact between the skin and the electrode is provided, which further improves the signal quality.

According to a further embodiment, at least a part of the bendable arm is a bendable behind the ear part adapted for extending to a behind the ear area, i.e. to the side of the auricle facing the head, when in use. Said bendable behind the ear part may be also provided as a further bendable arm. Said bendable behind the ear part further improves the fixing of the ear device at the ear of the person as well as the contact stability between electrodes and skin without the need of customization.

According to a preferred embodiment, the behind the ear part comprises at least one behind the ear electrode, and the behind the ear part is adapted to exert a pressure such that the at least one behind the ear electrode is pressed against the skin of the external ear and/or the head when in use. Thereby, a further electrode for measuring bioelectrical signals is provided at a larger distance to the at least one ear canal electrode, which further improves the signal quality without the need of customization. Likewise, the fixing of the ear device at the ear of the person as well as the contact stability between electrodes and skin is further improved without the need of customization.

According to a further embodiment, the external ear part comprises a cavity, in which an electrical wiring for connecting the external ear electrode and/or the behind the ear electrode is routed. Thereby, the cavity provides a particularly good and easy installation of the electrical wiring. Moreover, the cavity allows a simplified bending of the external ear part such that the external ear part with its at least one external ear electrode and/or at least one behind the ear electrode may easily apply a pressure against the skin, which further improves the signal quality without the need of customization.

According to a further embodiment, an angle between an axis of the ear canal part along the ear canal and a plane defined by the external ear part, in particular of the bendable arm, is adjustable according to the ear of the person. Thereby, the fitting of the ear device can be better adjusted to the specific form of the ear of the person. Preferably, said angle is lockable such the angle remains constant to ensure an improved and stabilized fitting of the ear device at the ear of the person. This further ensures the stable contact between electrodes and skin.

According to a further embodiment, the ear device further comprises an acoustic alarm module, which is configured to output an acoustic alarm signal depending on at least one detected bioelectrical signal. For example, in case of hypoglycemia, the person wearing the ear device can thus be warned about a low blood glucoselevel.

According to a further embodiment, there may be other sensor modalities included in the ear device (e.g. accelerometers, temperature sensors, body-coupled microphones, optical pulse oximetry, NIRS, etc.). Moreover, the ear device may comprise means for communicating with external devices.

According to a further embodiment, there is provided a set of ear devices, wherein the shape of the devices within the set is the same, but the sizes of the different devices are different. For example, an audiologist or another fitting person can thus easily select the best generic size of the device for a person wearing the device. The device can then finally be adapted to the specific ear form of the person by the deformable ear canal part and the bendable arm as described above. Thereby, providing a set of ear devices having different sizes but the same shape avoids customization of the ear device for a specific person.

In a preferred embodiment, a hearing assisting device or a headset comprises the ear device as defined in either one of the claims.

In another preferred embodiment, a bioelectrical signal monitor comprises the ear device as defined in either one of the claims.

BRIEF DESCRIPTION OF THE DRAWINGS

Embodiments of the invention will now be explained in further detail with reference to the figures.

DETAILED DESCRIPTION OF THE INVENTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details.

Figure 1:
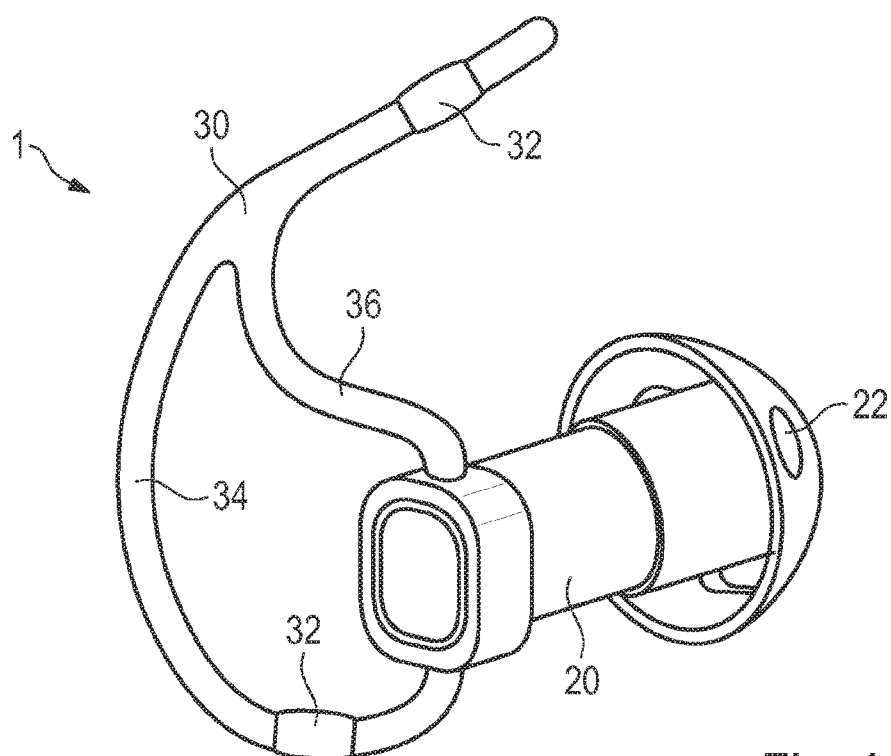
FIG. 1 illustrates an example of an ear device having electrodes.
Figure 2:
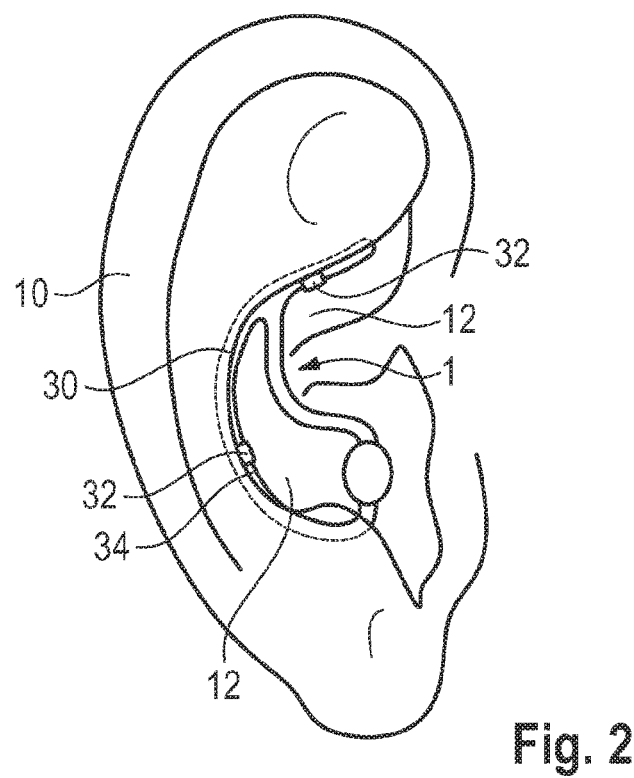
FIG. 2 illustrates an ear with an example of an ear device arranged in the ear canal and in the concha.
Figure 3:
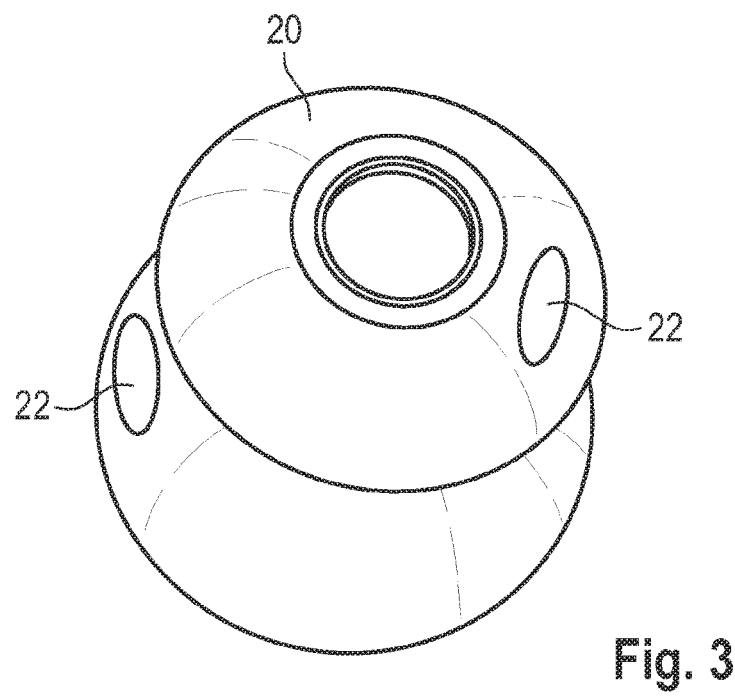
FIGS. 3 and 4 illustrate an example of an ear canal part of the ear device.
Figure 4:
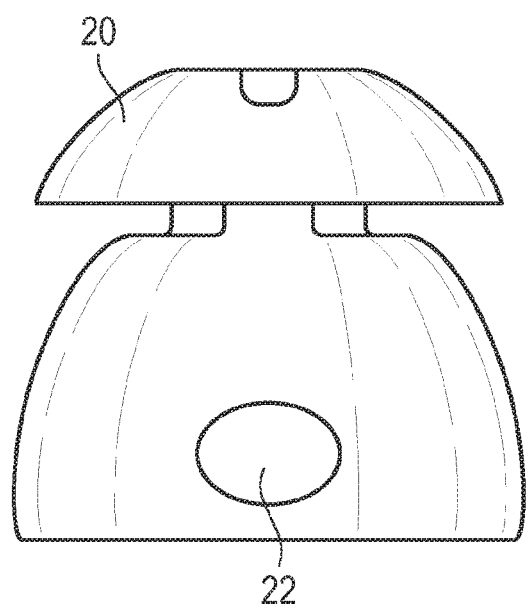
Figure 5:
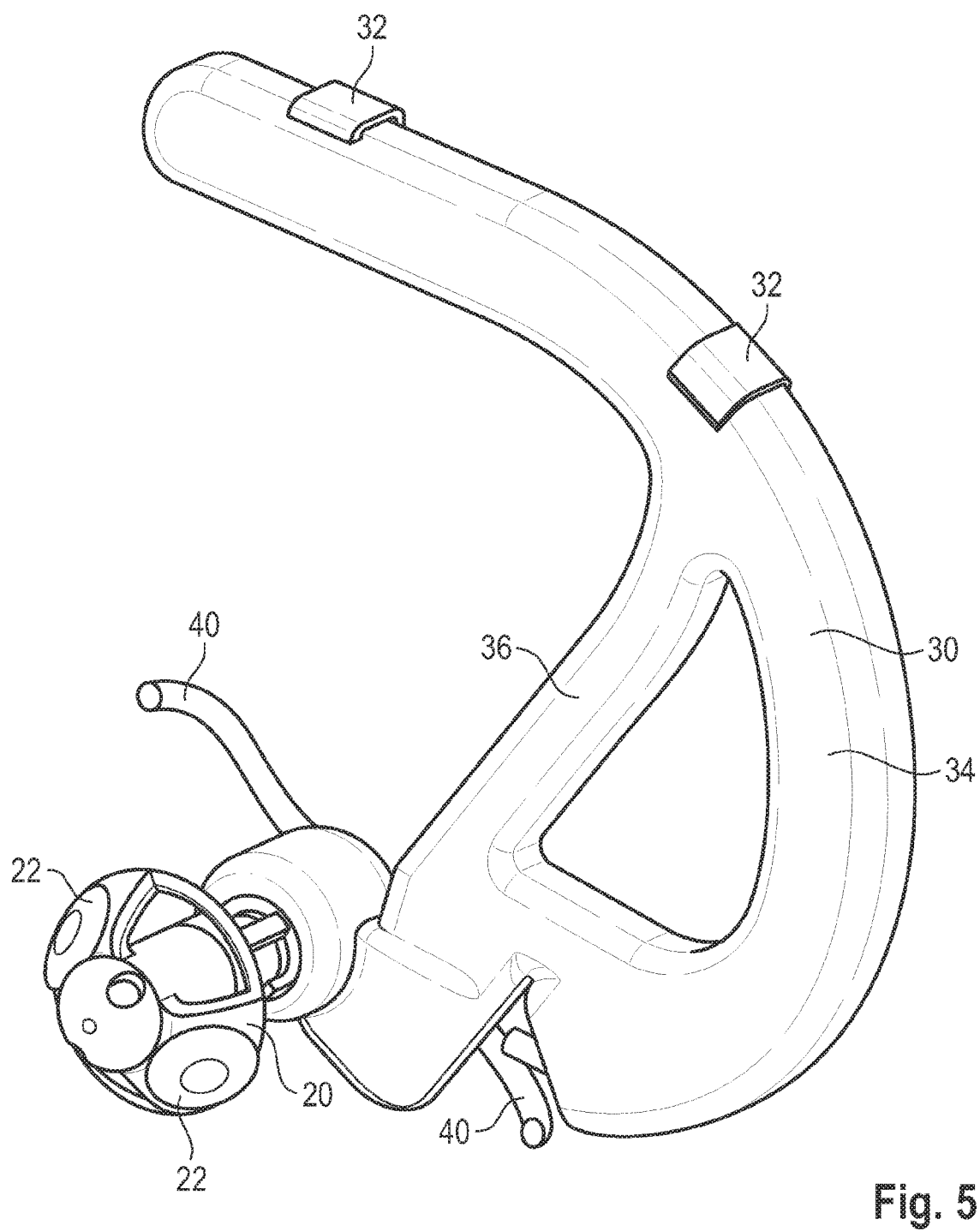
FIGS. 5 to 13 illustrate another example of an ear device.
Figure 6:
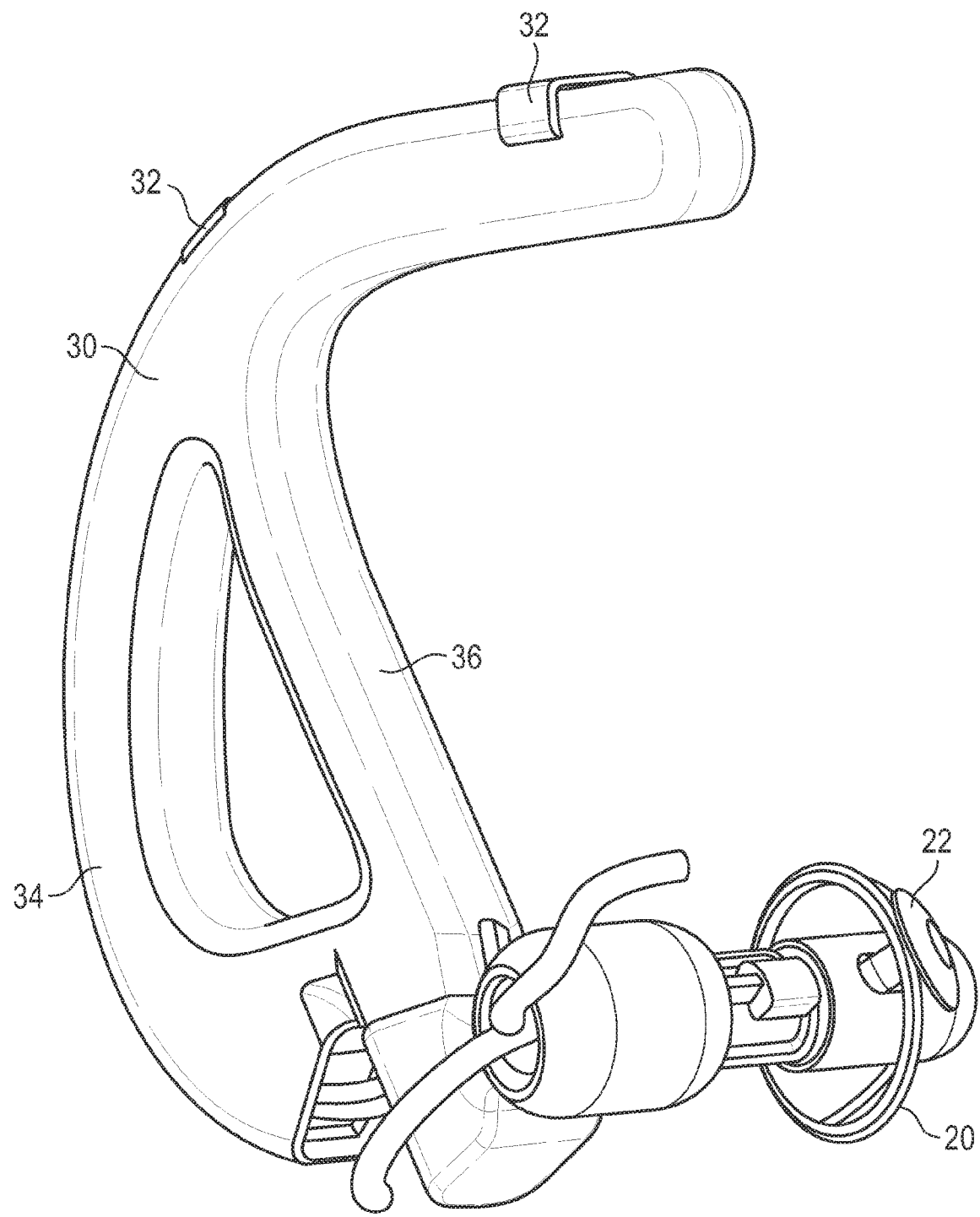

FIG. 1 shows an embodiment of an ear device 1 of the invention. The ear device 1 comprises an ear canal part 20, which is adapted to be arranged in an ear canal of an ear 10 of a person, see FIG. 2. The ear canal part 20 comprises at least one ear canal electrode 22. As shown in FIG. 3, the ear canal part 20 may comprise two ear canal electrodes 22. In principle, the number of ear canal electrodes 22 depends on the bioelectrical signal to be measured by the ear device 1. In general, preferred bioelectrical signals are for example EEG signals. However, the present invention may also be used in all the applications mentioned in the background section. FIG. 4 shows a side view of the ear canal part 20.

As shown in FIG. 1, the ear device 1 further comprises also an external ear part 30, which is adapted to be arranged external to the ear canal. The external ear part 30 comprises at least one external ear electrode 32. As shown in FIG. 1, the external ear part 30 may comprise two external ear electrodes 32. In principle, the number of external ear electrodes 32 depends on the bioelectrical signal to be measured by the ear device 1. In general, preferred bioelectrical signals are for example EEG signals.

Thereby, it is mentioned that the ear canal electrode 22 is optional in this embodiment. Using the ear canal electrode 22 and the external ear electrode 32 provides nevertheless an increased distance between the electrodes for measuring the bioelectrical signal. By this increased distance, the signal quality can be improved.

As shown in FIG. 1, the external ear part 30 comprises a bendable arm 34, which is connected to the ear canal part 20. As shown in FIG. 2, the bendable arm 34 provides a concha part, which is adapted to follow the shape of a concha 12 of the ear 10. Thereby, the concha part of the bendable arm 34 fits closely to at least one protrusion of the concha 12 and exerts thereby a pressure such that at least one of the external ear electrodes 32 is pressed against the skin of the person when in use. Moreover, a dislocation of the ear canal part 20 is thereby prevented, too.

As shown in FIG. 1, the external ear part 30 may further comprise a stabilizing arm 36, which may likewise be bendable as the bendable arm 34. The stabilizing arm 36 is adapted to further stabilize the bendable arm 34 such that the bendable arm 34 exerts a sufficient pressure against the concha 12.

Another example of the ear device 1 as shown in FIGS. 5 to 13. Thereby, the reference signs correspond to the features as explained with respect to FIGS. 1 to 4.

Figure 10:
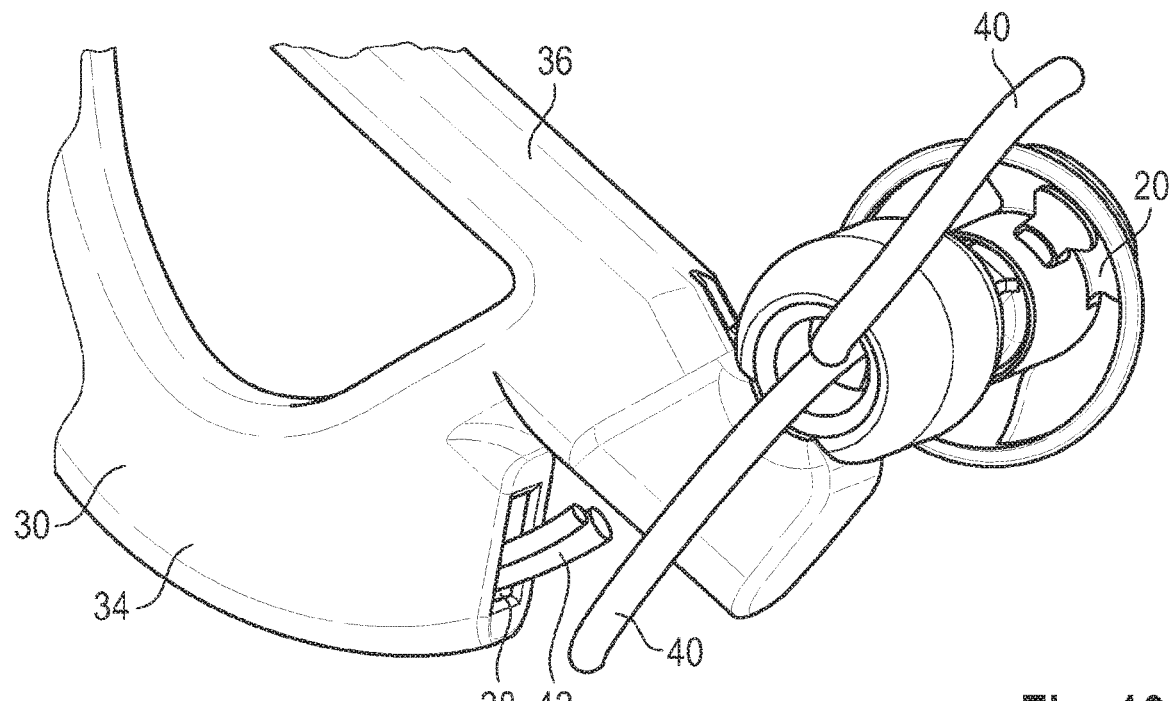
Figure 11:
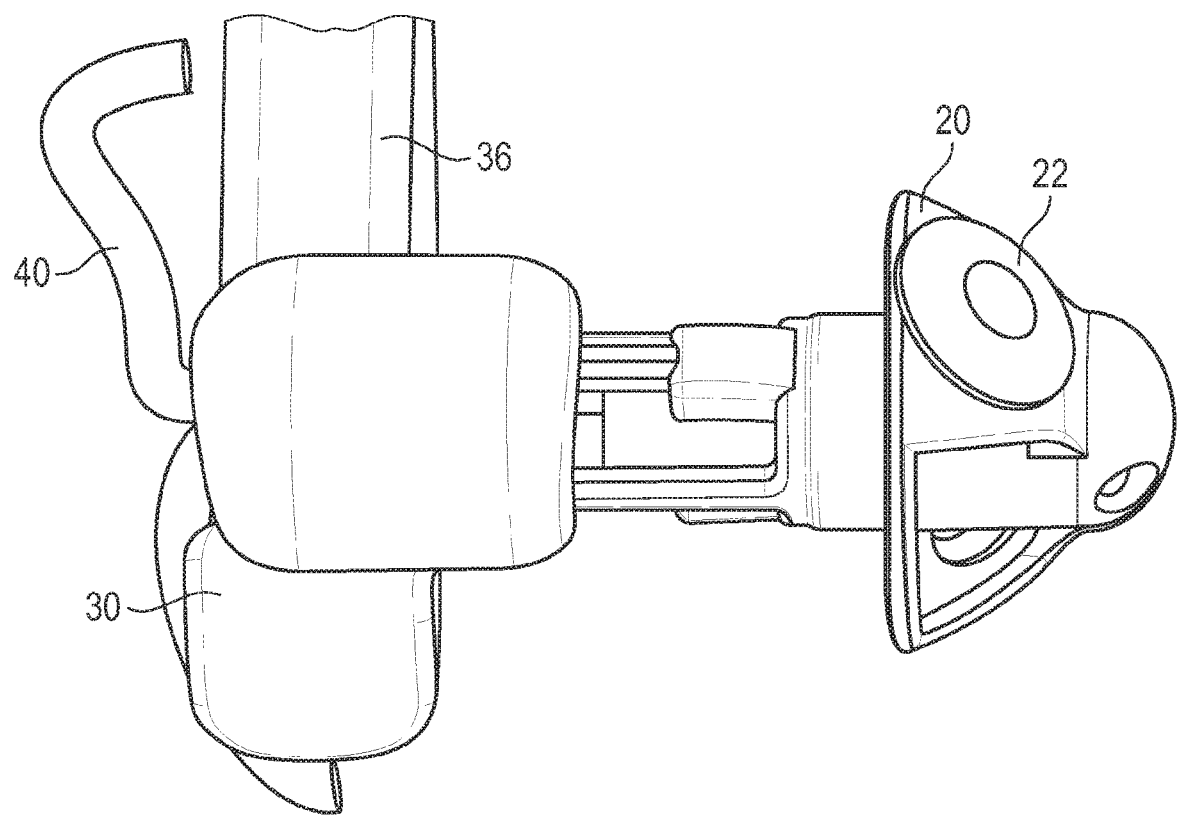
Figure 12:
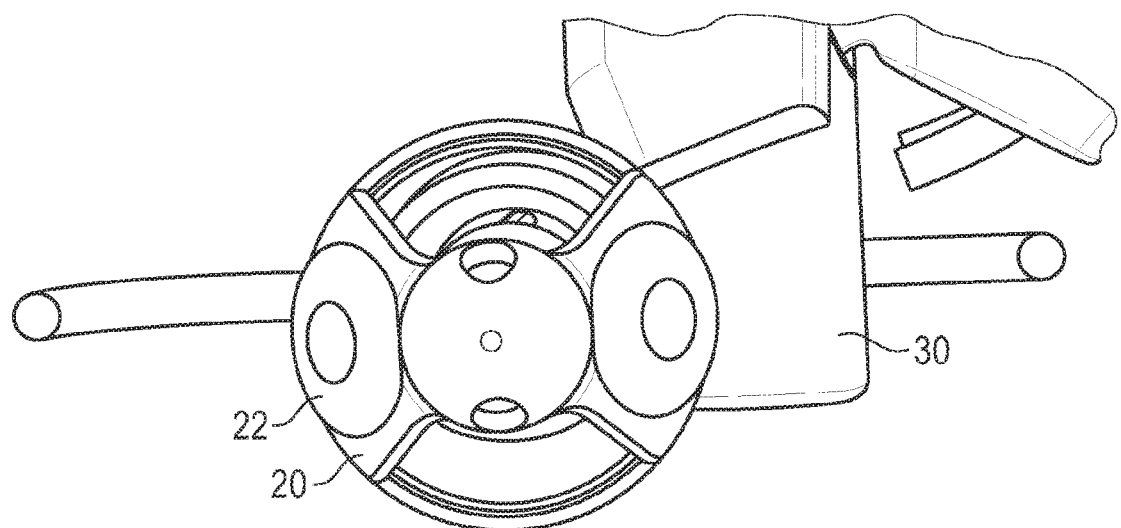
Figure 13:
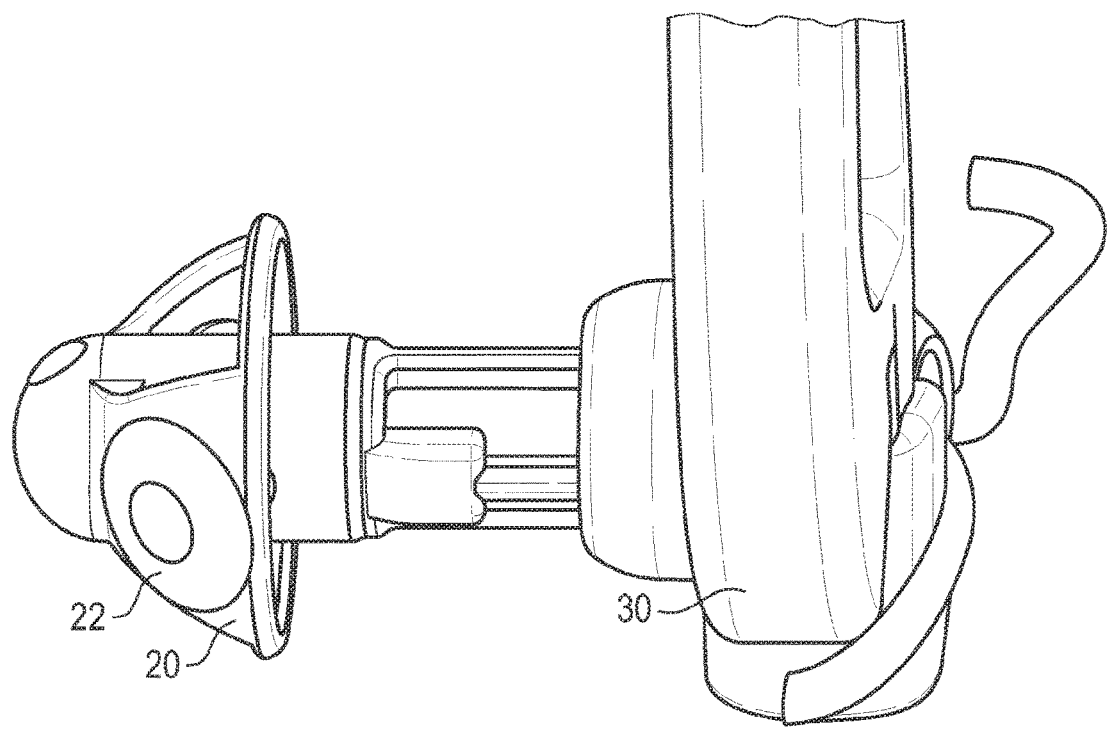

FIGS. 5 to 13 show further an ear canal part wiring 40. Moreover, FIG. 10 shows an external ear part wiring 42. These wirings 40 and 42 may be in contact with a detachable connection to a unit holding a bioelectrical signal processor and/or a power supply (not shown).

Thereby, FIG. 10 further shows that the external ear part wiring 42 is routed in a cavity 28 of the external ear part 30. The cavity 28 provides a particularly good and easy installation of the external ear part wiring 42. Moreover, the cavity 28 allows a simplified bending of the external ear part 30 such that the external ear part 30 with its at least one external ear electrode 32 may easily apply a pressure against the skin, which further improves the signal quality without the need of customization.

In summary, the ear device 1 can be arranged in the concha region 12, exerting a slight pressure in the concha 12 in order to both establish a good electrical contact between at least one of the electrodes 32 and the skin of the ear 10.

Furthermore, the ear device 1 may include or be in close connection with an electronic module for amplifying, performing analogue to digital conversion and e.g. filtering in order to improve the signal to noise ratio (not shown). The wiring 42 and 40 for guiding the bioelectrical signals from the electrodes and to this electronic module, is preferably shielded, e.g. in the form of a coax cable.

Such a wiring may be embedded, fully or partly, in the material forming the ear canal part. This will save space in the ear canal part, and will provide protection for these thin cables.

In general, the external ear part 30, which is adapted to be arranged at the ear external to the ear canal, can have different forms and shapes.

In one form, it can be arranged in the concha region as shown in FIG. 2, exerting a slight pressure in the concha in order to both establish a good electrical contact between an electrode and the skin.

In another form, the external ear part can extend towards or into the helix, triangular fossa, crura of antihelix or Scapha region where an electrode may be arranged.

Furthermore, an electrode placement at Tragus is preferred since this area allows for extra pressure by adding additional material to the bendable arm. Moreover, the tragus region often has a different potential than the concha region, as shown by measurements. This further improves the measurement of the bioelectrical signal.

Figure 14:
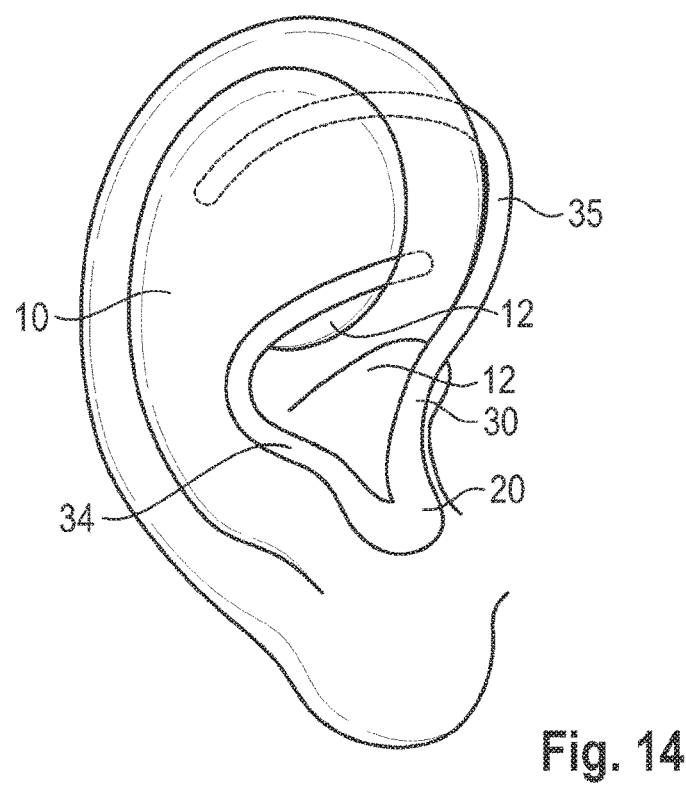
FIG. 14 illustrates an example of an ear device having a bendable arm with a concha part and a bendable arm with a behind the ear part.

In another form as shown in FIG. 14, the external ear part 30 may comprise a bendable behind the ear part 35 extending to the behind the ear space, i.e. to the cleft between the ear and the head. The bendable part 35 extending to behind the ear may be countered by a concha part, and these two parts of the thus branched, bendable arm 34 in combination may clamp the ear slightly in order to ensure a good electrical contact. The electrode can be arranged at either of two clamping parts, the part extending behind the ear (as at least one behind the ear electrode, not shown) and/or at a part in the concha (as external ear electrode 32). Thereby, the at least one behind the ear electrode may arranged on the bendable behind the ear part 35 such that this electrode contacts the ear and/or the head. For simplification, the ear canal part 20 is not shown in FIG. 14. Moreover, it is also possible that the external ear part 30 is only formed by the bendable behind the ear part 35.

In other words, the external ear part 30 may thus be formed to have several arms (like a spider). Some of the bendable arms may only serve the purpose of creating a counter-force to the force applied by the other arms. One embodiment is for example to have a fork-like structure in the Cymba cavity region, where one of the arms applies a pressure downwards and another arm applies a pressure upwards.

Having at least four electrodes offers the advantage of eliminating the risk that two or maybe three electrodes being arranged at the same equipotential line/surface such that no signal can be detected. The risk is small when three electrodes are provided, but can be eliminated when applying four or more electrodes.

Moreover, the optimal electrode positions depends on what it is intended to measure (because different physiological phenomenon's have different potential fields in the ear.) and/or the anatomical shape of the ear (in order to get a good and reliable contact). Thereby, there may be large inter-subject variation in both anatomy and physiology.

Therefore, it may be advantageous to provide ear device 1 with a multitude of electrodes, and then select the optimal sub-set of electrodes to be used, when the device is fitted to the patient/user.

Figure 7:
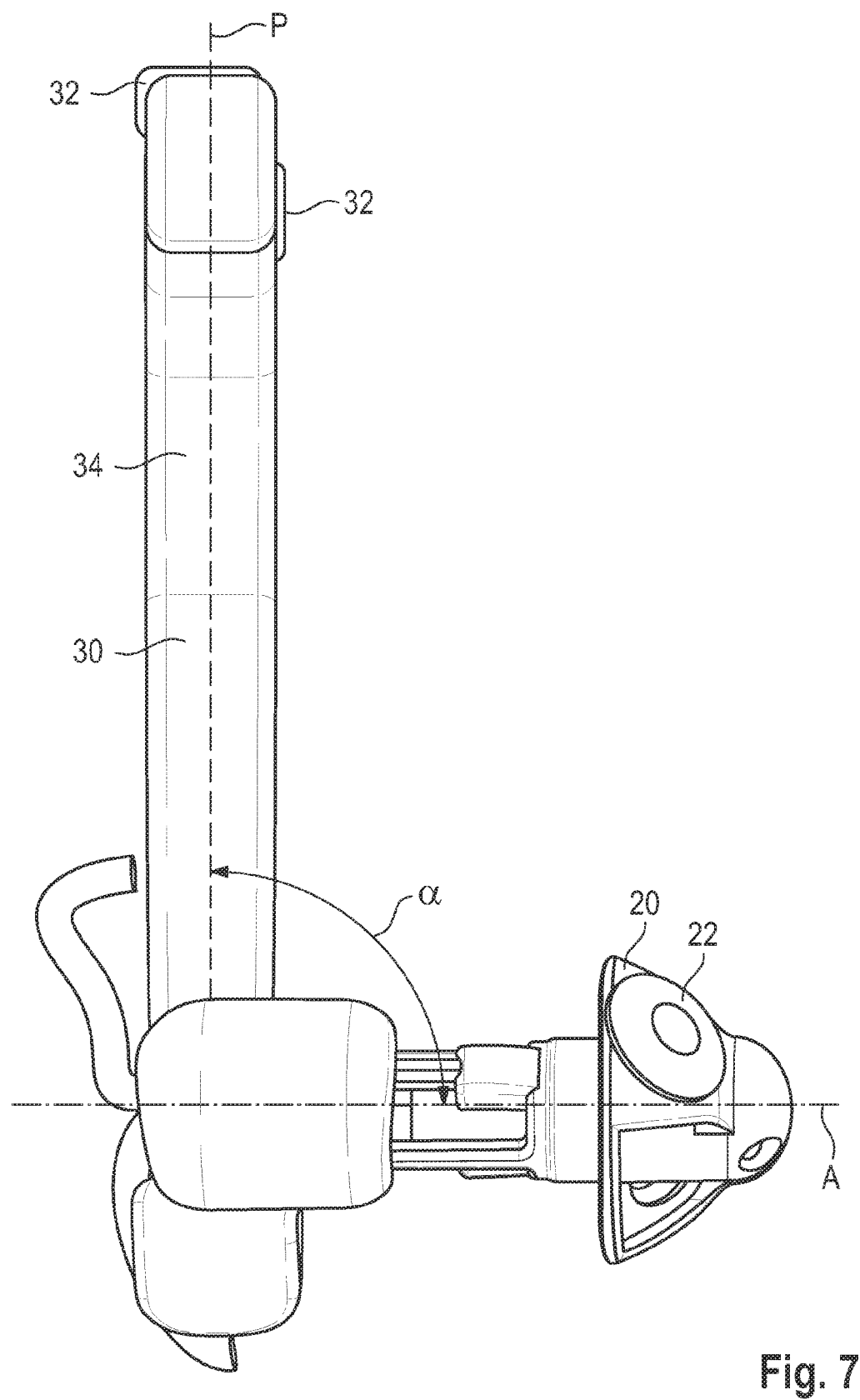
Figure 8:
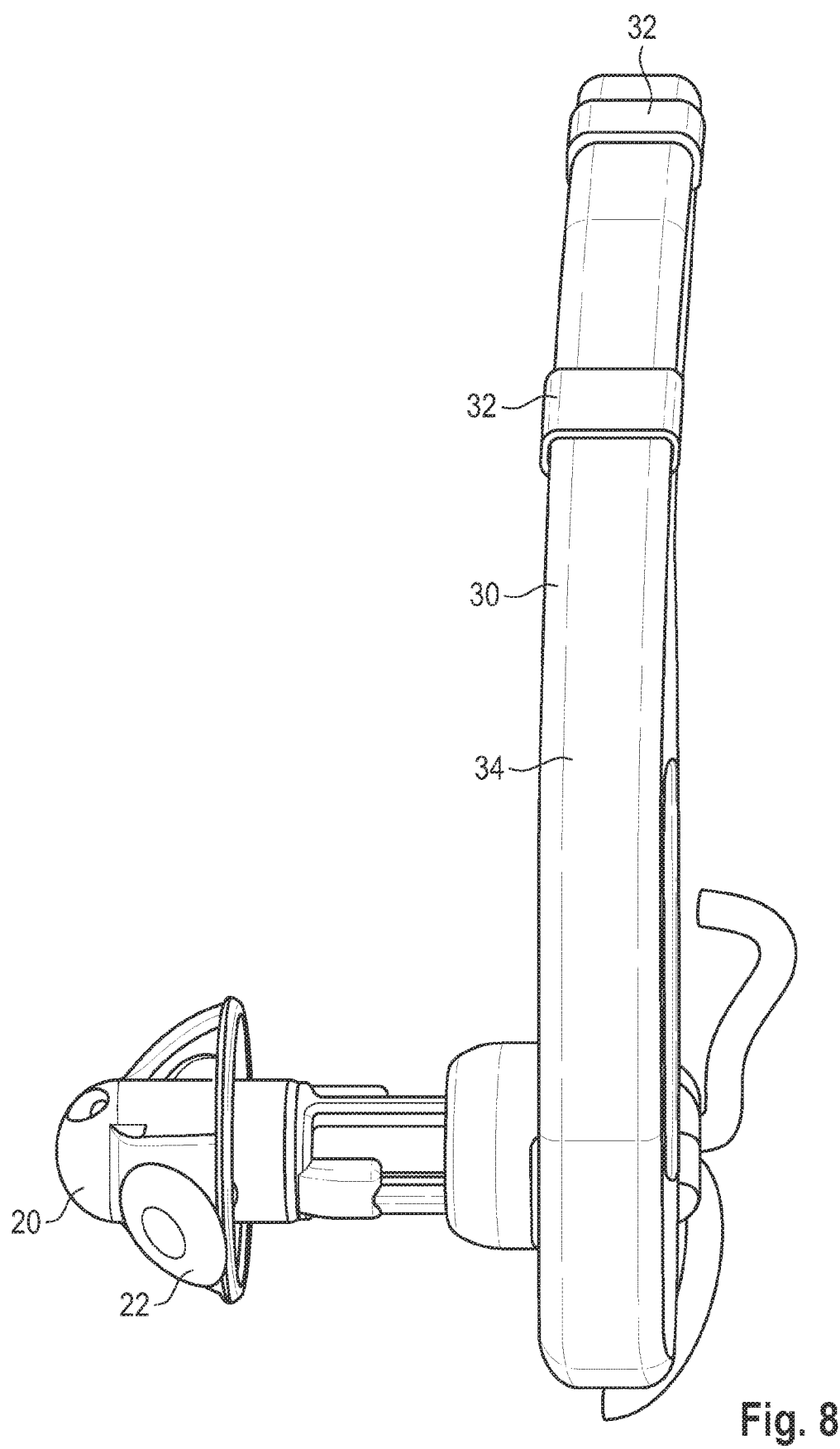
Figure 9:
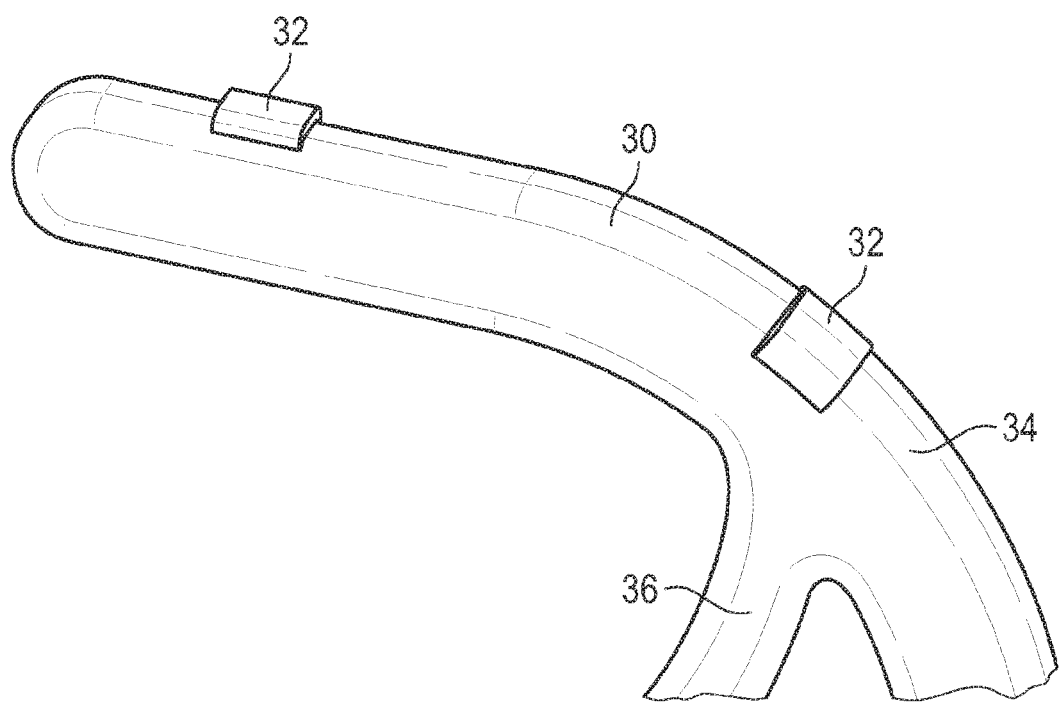

Often, the external ear part will extend in one plane. The ear canal part will typically extend along an axial direction approximately orthogonal to the plane defined by the external ear part. In this regard, FIG. 7 shows that the external ear part 30 defines a plane P (dashed line), in which the external ear part 30 is arranged, and the ear canal part 20 defines an axis A (dotted line) along the ear canal. An angle α between this plane P and the axis A should preferably be adjustable, such that it can be adapted easily to an individual who needs to carry the device. Thereby, the ear canal part is preferably flexible, which means that it can be hinged around angles (2-DOF). Thereby, the comfort during wearing the ear device is further improved and a customization is not necessary as generic and adjustable parts may be used for different persons.

In general, the ear canal part 20 and the external ear part 30, in particular the bendable arm 34 and the bendable behind the ear part 35, are preferably made of elastic or viscoelastic and biocompatible materials, such as silicone or rubbers, and may also be coated with foams or other suitable coatings. "Bendable" is thereby to be understood as elastic and flexible. These components are thus adapted to exert a pressure such that the corresponding electrodes are pressed against the skin when in use. Thereby, a customization is not necessary as generic parts may be used for different persons as discussed above.

This further allows to provide a set of ear devices 1, which have the same shape but different sizes (not shown).

Furthermore, the acoustic alarm module may preferably be received in the ear canal part.

Finally, the ear device 1 can be used within a hearing assisting device (not shown). Thereby, a transducer, a DSP or any other components of a hearing device may for example be provided together with the ear canal part 20 in the ear canal. If needed, components of the hearing device may also be provided behind the ear 10.

Further implementations are summarized in the following examples:

Example 1: An ear device for arrangement at an ear of a person and provided with at least two electrodes for having skin contact and detecting a bioelectrical signal when in use, the ear device comprises
  a deformable ear canal part adapted to be arranged in an ear canal of the person, and
  an external ear part adapted to be arranged at the ear external to the ear canal and being provided with at least one external ear electrode for detecting a bioelectrical signal, the external ear part comprises at least one bendable arm which is connected to the ear canal part and is adapted to exert a pressure such that the at least one external ear electrode is pressed against the skin when in use.

Example 2: The ear device according to example 1, wherein the ear canal part is provided with at least one ear canal electrode for detecting a bioelectrical signal, the at least one ear canal electrode is arranged at a structure adapted to be deformed when the ear canal part is arranged in an ear canal, such that the at least one ear canal electrode is pressed against the skin of the ear canal.

Example 3: The ear device according to any one of the previous examples, wherein the ear canal part is formed such that it only has contact to an upper part of the ear canal when in use.

Example 4: The ear device according to any one of the previous examples, wherein at least a part of the bendable arm is a concha part adapted to be arranged in a concha region of the ear and further adapted to follow the shape of the concha, wherein preferably the bendable arm is extending from the ear canal part to at least a point in the concha, where the at least one external ear electrode is held.

Example 5: The ear device according to any one of the previous examples, wherein at least a part of the bendable arm is a tragus part adapted to be arranged in a tragus region of the ear and further adapted to follow the shape of the tragus, wherein preferably the bendable arm is extending from the ear canal part to at least a point at the tragus, where the at least one external ear electrode is held.

Example 6: The ear device according to any one of the previous examples, comprising a detachable connection to a unit holding a bioelectrical signal processor and a power supply.

Example 7: The ear device according to any one of the previous examples, wherein the bioelectrical signal is an EEG signal.

Example 8: The ear device according to any one of the previous examples, wherein the bendable arm is adapted to hold the at least one external ear electrode.

Example 9: The ear device according to any one of the previous examples, wherein at least a part of the bendable arm is a bendable behind the ear part adapted for extending to a behind the ear area, i.e. to the side of the auricle facing the head, when in use.

Example 10: The ear device according to example 9, wherein the behind the ear part comprises at least one behind the ear electrode, and the behind the ear part is adapted to exert a pressure such that the at least one behind the ear electrode is pressed against the skin of the external ear and/or the head when in use.

Example 11: The ear device according to any one of the previous examples, wherein the external ear part comprises a cavity, in which an electrical wiring for connecting the external ear electrode and/or the behind the ear electrode is routed.

Example 12: The ear device according to any one of the previous examples, wherein an angle between an axis of the ear canal part along the ear canal and a plane defined by the external ear part, in particular of the bendable arm, is adjustable according to the ear of the person, wherein preferably said angle is lockable.

Example 13: The ear device according to any one of the previous examples, wherein the ear device further comprises an acoustic alarm module, which is configured to output an acoustic alarm signal depending on at least one detected bioelectrical signal.

Example 14: A set of ear devices according to any one of the preceding examples, wherein the shape of the devices within the set is the same, but the sizes of the different devices are different.

Example 15: A hearing assisting device or a headset comprising the ear device according to any one of the preceding examples.

Example 16: A bioelectrical signal monitor comprising the ear device according to any one of the preceding examples 1 to 14.

The invention claimed is:

1. An ear device for arrangement at an ear of a person and provided with at least two electrodes for having skin contact and detecting a bioelectrical signal when in use, the ear device comprises a deformable ear canal part adapted to be arranged in an ear canal of the person, and an external ear part adapted to be arranged at the ear external to the ear canal and being provided with at least one external ear electrode for detecting a bioelectrical signal, the external ear part comprises at least one bendable arm which is connected to the ear canal part and is adapted to exert a pressure such that the at least one external ear electrode is pressed against the skin when in use, wherein said bendable arm includes at least one of (i) a concha part adapted to be arranged in a concha region of the ear and further adapted to follow the shape of the concha, wherein preferably the bendable arm is extending from the ear canal part to at least a point in the concha where the at least one external ear electrode is held, with at least a portion of the bendable arm between the ear canal part and said point in the concha being bendable, and (ii) a tragus part adapted to be arranged in a tragus region of the ear and further adapted to follow the shape of the tragus, wherein preferably the bendable arm is extending from the ear canal part to at least a point at the tragus where the at least one external ear electrode is held, with at least a portion of the bendable arm between the ear canal part and said point at the tragus being bendable.

2. The ear device according to claim 1, wherein the ear canal part is provided with at least one ear canal electrode for detecting a bioelectrical signal, the at least one ear canal electrode is arranged at a structure adapted to be deformed when the ear canal part is arranged in an ear canal, such that the at least one ear canal electrode is pressed against the skin of the ear canal.

3. The ear device according to claim 1, wherein the ear canal part is formed such that it only has contact to an upper part of the ear canal when in use.

4. The ear device according to claim 1, wherein at least a part of the bendable arm is a concha part adapted to be arranged in a concha region of the ear and further adapted to follow the shape of the concha, wherein preferably the bendable arm is extending from the ear canal part to at least a point in the concha, where the at least one external ear electrode is held.

5. The ear device according to claim 1, wherein at least a part of the bendable arm is a tragus part adapted to be arranged in a tragus region of the ear and further adapted to follow the shape of the tragus, wherein preferably the bendable arm is extending from the ear canal part to at least a point at the tragus, where the at least one external ear electrode is held.

6. The ear device according to claim 1, comprising a detachable connection to a unit holding a bioelectrical signal processor and a power supply.

7. The ear device according to claim 1, wherein the bioelectrical signal is an EEG signal.

8. The ear device according to claim 1, wherein the bendable arm is adapted to hold the at least one external ear electrode.

9. The ear device according to claim 1, wherein at least a part of the bendable arm is a bendable behind the ear part adapted for extending to a behind the ear area, i.e. to the side of the auricle facing the head, when in use.

10. The ear device according to claim 9, wherein the behind the ear part comprises at least one behind the ear electrode, and the behind the ear part is adapted to exert a pressure such that the at least one behind the ear electrode is pressed against the skin of the external ear and/or the head when in use.

11. The ear device according to claim 1, wherein the external ear part comprises a cavity, in which an electrical wiring for connecting the external ear electrode and/or the behind the ear electrode is routed.

12. The ear device according to claim 1, wherein an angle between an axis of the ear canal part along the ear canal and a plane defined by the external ear part, in particular of the bendable arm, is adjustable according to the ear of the person, wherein said angle is lockable.

13. The ear device according to claim 1, wherein the ear device further comprises an acoustic alarm module, which is configured to output an acoustic alarm signal depending on at least one detected bioelectrical signal.

14. The ear device according to claim 1, wherein the ear canal part is provided with at least one ear canal electrode for detecting a bioelectrical signal, the at least one ear canal electrode is arranged at a structure adapted to be deformed when the ear canal part is arranged in an ear canal, such that the at least one ear canal electrode is pressed against the skin of the ear canal, wherein the ear canal part is formed such that it only has contact to an upper part of the ear canal when in use.

15. The ear device according to claim 1, wherein the ear canal part is formed such that it only has contact to an upper part of the ear canal when in use and wherein at least a part of the bendable arm is a concha part adapted to be arranged in a concha region of the ear and further adapted to follow the shape of the concha, wherein preferably the bendable arm is extending from the ear canal part to at least a point in the concha, where the at least one external ear electrode is held.

16. The ear device according to claim 1, wherein the ear canal part is formed such that it only has contact to an upper part of the ear canal when in use and wherein at least a part of the bendable arm is a tragus part adapted to be arranged in a tragus region of the ear and further adapted to follow the shape of the tragus, wherein preferably the bendable arm is extending from the ear canal part to at least a point at the tragus, where the at least one external ear electrode is held.

17. The ear device according to claim 1, wherein the ear canal part is formed such that it only has contact to an upper part of the ear canal when in use and wherein at least a part of the bendable arm is a bendable behind the ear part adapted for extending to a behind the ear area, i.e. to the side of the auricle facing the head, when in use, wherein preferably the behind the ear part comprises at least one behind the ear electrode, and the behind the ear part is adapted to exert a pressure such that the at least one behind the ear electrode is pressed against the skin of the external ear and/or the head when in use.

18. The ear device according to claim 1, wherein at least a part of the bendable arm is a concha part adapted to be arranged in a concha region of the ear and further adapted to follow the shape of the concha, wherein preferably the bendable arm is extending from the ear canal part to at least a point in the concha, where the at least one external ear electrode is held and wherein at least a part of the bendable arm is a tragus part adapted to be arranged in a tragus region of the ear and further adapted to follow the shape of the tragus, wherein preferably the bendable arm is extending from the ear canal part to at least a point at the tragus, where the at least one external ear electrode is held.

19. The ear device according to claim 1, wherein at least a part of the bendable arm is a concha part adapted to be arranged in a concha region of the ear and further adapted to follow the shape of the concha, wherein preferably the bendable arm is extending from the ear canal part to at least a point in the concha, where the at least one external ear electrode is held and wherein at least a part of the bendable arm is a bendable behind the ear part adapted for extending to a behind the ear area, i.e. to the side of the auricle facing the head, when in use, wherein preferably the behind the ear part comprises at least one behind the ear electrode, and the behind the ear part is adapted to exert a pressure such that the at least one behind the ear electrode is pressed against the skin of the external ear and/or the head when in use.

20. The ear device according to claim 1, wherein at least a part of the bendable arm is a tragus part adapted to be arranged in a tragus region of the ear and further adapted to follow the shape of the tragus, wherein preferably the bendable arm is extending from the ear canal part to at least a point at the tragus, where the at least one external ear electrode is held and wherein at least a part of the bendable arm is a bendable behind the ear part adapted for extending to a behind the ear area, i.e. to the side of the auricle facing the head, when in use, wherein preferably the behind the ear part comprises at least one behind the ear electrode, and the behind the ear part is adapted to exert a pressure such that the at least one behind the ear electrode is pressed against the skin of the external ear and/or the head when in use.

21. The ear device according to claim 1, wherein the ear canal part is formed such that it only has contact to an upper part of the ear canal when in use, and wherein at least a part of the bendable arm is a concha part adapted to be arranged in a concha region of the ear and further adapted to follow the shape of the concha, wherein preferably the bendable arm is extending from the ear canal part to at least a point in the concha, where the at least one external ear electrode is held, and wherein at least a part of the bendable arm is a tragus part adapted to be arranged in a tragus region of the ear and further adapted to follow the shape of the tragus, wherein preferably the bendable arm is extending from the ear canal part to at least a point at the tragus, where the at least one external ear electrode is held, and wherein at least a part of the bendable arm is a bendable behind the ear part adapted for extending to a behind the ear area, i.e. to the side of the auricle facing the head, when in use, wherein preferably the behind the ear part comprises at least one behind the ear electrode, and the behind the ear part is adapted to exert a pressure such that the at least one behind the ear electrode is pressed against the skin of the external ear and/or the head when in use.

22. A hearing assisting device or a headset comprising the ear device according to claim 1.

23. A bioelectrical signal monitor comprising the ear device according to claim 1.

* * * * *